US008126740B2

(12) United States Patent
Busch (10) Patent No.: US 8,126,740 B2
(45) Date of Patent: Feb. 28, 2012

(54) ELECTRONIC HEALTH RECORD CASE MANAGEMENT SYSTEM

(76) Inventor: Rebecca S. Busch, Clarendon Hills, IL (US)

( * ) Notice: Subject to any disclaimer, the term of this patent is extended or adjusted under 35 U.S.C. 154(b) by 231 days.

(21) Appl. No.: 12/384,033

(22) Filed: Mar. 30, 2009

(65) Prior Publication Data

US 2009/0259491 A1    Oct. 15, 2009

Related U.S. Application Data

(60) Provisional application No. 61/072,217, filed on Mar. 28, 2008.

(51) Int. Cl.
*G06Q 50/00* (2012.01)
(52) U.S. Cl. .............................. 705/3; 705/2
(58) Field of Classification Search ............. 705/2–4
See application file for complete search history.

(56) References Cited

U.S. PATENT DOCUMENTS

| | | | | | |
|---|---|---|---|---|---|
| 5,823,948 A | * | 10/1998 | Ross et al. | ............ | 600/300 |
| 7,686,214 B1 | * | 3/2010 | Shao et al. | ............ | 235/380 |
| 2002/0026332 A1 | * | 2/2002 | Snowden et al. | ............ | 705/3 |
| 2002/0143577 A1 | * | 10/2002 | Shiffman et al. | ............ | 705/2 |
| 2002/0165736 A1 | * | 11/2002 | Tolle et al. | ............ | 705/3 |
| 2003/0167190 A1 | * | 9/2003 | Rincavage et al. | ............ | 705/3 |
| 2004/0078228 A1 | * | 4/2004 | Fitzgerald et al. | ............ | 705/2 |
| 2005/0071194 A1 | * | 3/2005 | Bormann et al. | ............ | 705/2 |
| 2007/0112598 A1 | * | 5/2007 | Heckerman et al. | ............ | 705/2 |

\* cited by examiner

*Primary Examiner* — Gerald J. O'Connor
*Assistant Examiner* — Sind Phongsvirajati
(74) *Attorney, Agent, or Firm* — Ryndak & Suri LLP (57) ABSTRACT

A method and system for transparent recording, storing, and accessing financial, clinical, and data/information case management services. The method includes collecting service data pertaining to a customer from a plurality of sources, storing the data, and providing multiple points of access to the data for retrieval by an individual via a user interface. A decision-support system may operate independently as an electronic health record or in conjunction with an integrated electronic health record and allows customers or their representatives to plan, facilitate, and monitor the management of financial, clinical, and data/information issues pertaining to their healthcare. In particular, the system is adapted to identify data tending to indicate an anomaly in the customer's health record and facilitate the selection and implementation of one or more options to address and/or correct the anomaly.

8 Claims, 7 Drawing Sheets

ELECTRONIC HEALTH RECORD CASE MANAGEMENT SYSTEM

CROSS REFERENCE TO RELATED APPLICATION

This application claims the benefit under 35 U.S.C. §119 (e) of U.S. Provisional Patent Application No. 61/072,217, filed Mar. 28, 2008, the disclosure of which is hereby incorporated in its entirety.

FIELD OF THE INVENTION

The present invention relates to systems and methods for integrating transparent financial, clinical, access and data/information case management services into an electronic health record.

BACKGROUND OF THE INVENTION

The U.S. healthcare market is in a state of crisis from a financial, clinical, and access perspective. Although numerous discussions in the literature and in the press focus on funding and access to healthcare the market conflict exists in the actual delivery of healthcare. It is not structured to manage patients' access and financial components as part of the process. To illustrate this point a review of key operating statements should be noted:

First, the professional standards association for case managers, "The American Management Society of America," defines the role of case management as "improv[ing] patient well-being and health care outcomes by supporting the professional development of care managers from a variety of disciplines, practice settings, skill levels and professional capacities." "Care managers" are further defined as "advocates who help patients understand their current health status, what they can do about it and why those treatments are important" and "catalysts [who guide] patients and provid[e] cohesion to other professionals in the health care delivery team, enabling their clients to achieve goals more effectively and efficiently." In reality, however, the healthcare market significantly falls short of integrating both clinical and financial case management as a defined process.

An extension of this concept and market conflict issue exists within the mission statement for the Department of Health and Human Services: "The Department of Health and Human Services (HHS) is the United States government's principal agency for protecting the health of all Americans and providing essential human services, especially for those who are least able to help themselves." This mission statement does not address financial management nor access as a discipline.

In contrast, the mission statement for the Department of Education notes the following: "Establishing policies on federal financial aid for education, and distributing as well as monitoring those funds. Collecting data on America's schools and disseminating research. Focusing national attention on key educational issues. Prohibiting discrimination and ensuring equal access to education." Access is addressed, unlike in healthcare.

The market conflict exists in the existence tools for the transparent financing of healthcare, clinical integration of, and access to healthcare. It is missing from two critical organizations within our market place on the public side DHHS and from a professional perspective CMSA. So the healthcare market as it exists today although often discussed from an application perspective financial case management as a discipline is not integrated within our delivery system.

The current investigation of Ingenix, a financial data base utilized by many payers, further highlights the market problem of healthcare from a financial perspective. Attorney General Mario Cuomo has identified monetary misrepresentations specifically in the out-of-network private payer world. This is just the beginning of the problem in that the market generating and utilizing financial data is biased and unreliable. The consumer and the healthcare providers do not have access to any reliable method or source of correlating financial data with clinical data. The most significant market problem is that the private payer market views the actual payment of a healthcare service to a provider in contrast to the amount charged back to an employer sponsored benefit plan as proprietary. The unique aspect to this invention is the methodology to create transparency. Transparency does not exist in the private sector. Other market issues with respect to health care waste fraud and abuse can be found in HHS literature available online.

Figure 1:
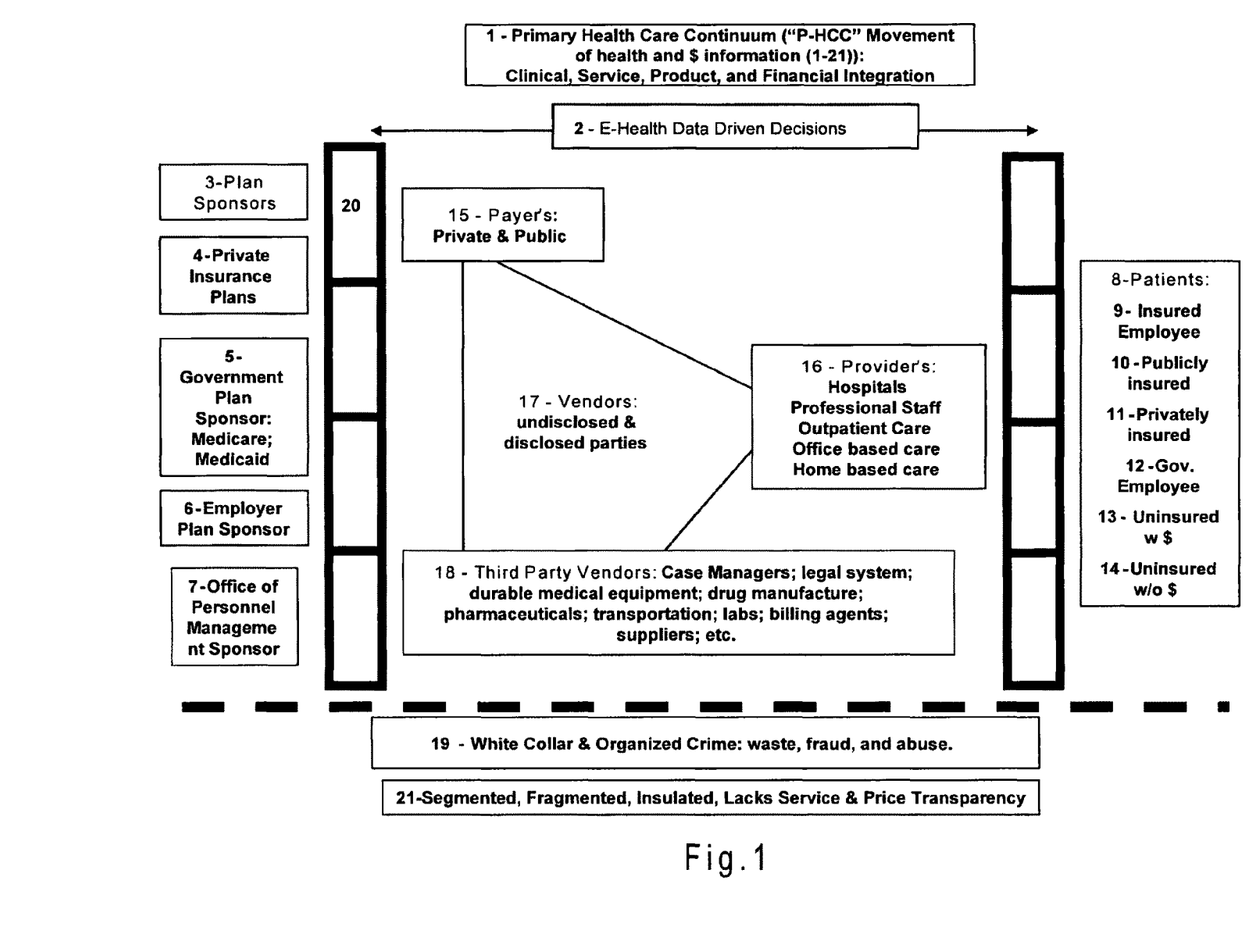
FIG. 1 illustrates the whole and sub parts of the primary healthcare continuum (P-HCC) of intermittent and contemporaneous financial, clinical, service, and product information and its concurrent and cyclical movement amongst and between licit and illicit market entities.

Further compounding the market problem of a lack of transparency are the segments of white collar and organized crime noted in FIG. 1. The ability for ethically challenged market members or entities to execute a theme is significantly higher in an industry in which the concept of monetary transactions is considered proprietary. For example, a payer can contract on what they will pay for a healthcare service on behalf of a plan sponsor. A payer can contract on what it will charge back for the service rendered on a healthcare service. However, neither the plan sponsor nor the provider is privy to the payment transactions. This compounds data analytics on usual and customary pricing in addition to services associated by price, further creating the need for an invention of a transparent data driven decision support system that integrates financial, clinical, and access components.

A need therefore exists for a transparent and reliable decision-support system enabling patients and healthcare professionals to effectively manage and control the healthcare experience from integrated a clinical, access, and financial perspective.

BRIEF SUMMARY OF THE INVENTION

In one aspect, the present invention provides a system for identifying and addressing anomalies in a customer's health records comprising a device encoded with logic; a display; an input device; a data storage device; and a processor. The processor is adapted to execute the logic to: collect fragmented data from a plurality of data sources; convert the fragmented data to a unified electronic format; merge the converted data into a data library in the data storage device; apply an algorithm to the unified and merged data to identify data indicating an anomaly; route the anomalous data to a decision matrix corresponding to a type of anomaly identified and to a list of options for addressing the type of anomaly; output a message to a user indicating the type of anomaly and listing the options for addressing the type of anomaly on the display; receive a decision selected by the user operating the input device; and store the decision selected by the user in the data library.

In another aspect, the present invention provides a method of identifying and correcting medical anomalies in a customer's health records comprising providing a system in accordance with the first aspect; receiving a message from the system indicating that a medical anomaly in the customer's health records was identified and listing options for addressing the medical anomaly; selecting an option from the listed options and inputting the selection; and providing treatment to the customer to correct the medical anomaly in accordance with the selected option.

DETAILED DESCRIPTION OF THE INVENTION

In this section, a method and system are disclosed for transparent recording, storing, and accessing financial, clinical, and data/information case management services. The method includes collecting service data from an individual, storing the data, and providing multiple points of access to the data for retrieval by an individual via a user interface. The decision-support system may operate independently as an electronic health record or in conjunction with an integrated electronic health record and allows users to plan, facilitate, and monitor the management of financial, clinical, and data/information issues pertaining to their healthcare.

The electronic health record case management system manages correct unfiltered non-contracted proprietary market health information resulting in transparent, financial, clinical, and data/information transparency of healthcare related transactions for users throughout the healthcare continuum (HCC). This system provides the healthcare market with an effective tool to transform, manage and utilize an accessible centralized corrected financial and clinical health information repository. Users are not limited to but include patients, benefit plan sponsors, providers, payers, and third party vendors. The transparency of information created by the electronic health record management system provides a foundation to integrate financial, clinical, service, and product information into a multitude of electronic data-driven processes and decisions; and to identify, analyze, and/or prevent medical and financial errors, medical identity theft, and/or waste, fraud, and abuse.

The electronic health record case management system engine is a retrospective, concurrent, prospective user tool for analytics, customized and analytic-driven decision trees, and self advocacy. The tool employs certain specific data elements from verbal, facsimile, electronic, and paper transactions that follow a certain specific set of algorithms to provide users with a comprehensive understanding of "who, what, when, where, why, and how" at any given time during a healthcare episode and facilitate data driven decisions. It is a comprehensive action-driven private, confidential, secure, portable personal diary and blue print of health and related financial information. Authorized sharing of information and data between and among users occurs within the information continuum (IC) through data interoperability drivers such as the internet, intranet, and extranet systems.

The electronic health record case management system helps guide patients through the complexities of the fragmented and conflicted health care system through self advocacy procedures based upon captured organized information to ensure selection of optimal clinical and cost effective healthcare services and mitigate exposure to errors, waste, fraud, and abuse. The system also allows users to efficiently perform investigations, exception evaluations, and forensic data analysis of collected health and financial data.

The electronic health record case management system engine uses claims data from claim forms including, but not limited to, UB-04, CMS-1500, ADA Dental Claim, pharmaceutical claim, durable medical equipment claim and/or respective country international claim forms, for health record data elements to capture health, financial, clinical, demographic, operational, policy and other information that feed electronic data analysis (EDA) to derive data intelligence. User instruction provides key market understanding and guidance to improve data-driven decision making.

As illustrated in FIG. 1, various resources feed integrated financial, clinical, service, and product healthcare data to the electronic health record case management system of the invention. These data resources include patients 8-14; plan sponsors 3-7 that fund health benefit programs; payers 15, i.e., entities that process payments for patients' professional and facility healthcare; healthcare providers 16; third-party vendors 18; and undisclosed vendors 17 that support any of the other market players identified herein. The system addresses white collar and organized crime activity 19 that exists within the healthcare continuum by specifically creating transparent decision support methodologies that will identify anomalies that are generated from white collar and organized crime activity. For example, if a patient is non responsive to a medication—is it because it is counterfeit versus the incorrect dosage? Integrating public health data such as theft of pharmaceutical inventory would provide an alert status of a medication type that is compromised, as indicated in FIG. 1 activity 19.

The invention also addresses the market problems of segmentation and fragmentation. As illustrated schematically in FIG. 1, barriers 20 exist within the healthcare continuum. The system accounts for the nature 21 of the data in the healthcare continuum's data environment by creating data filters to remove segmented, fragmented, insulated, and non transparent service and price. According to the present invention, electronic data-driven decisions 2 within the healthcare continuum are provided to target data of nature 21. For example, a case manager may respond to the alert "theft" combined with pricing outcome data of counterfeit Lipitor (a cholesterol reducing medication) by repeating a laboratory test for cholesterol levels in addition to inspecting the medication and its packaging. The integration of financing Lipitor as an ongoing treatment regimen will result in transparent plan sponsor data and their options from various pharmacy vendors. This procedure is not included in the existing methodology of case managers.

Figure 2:
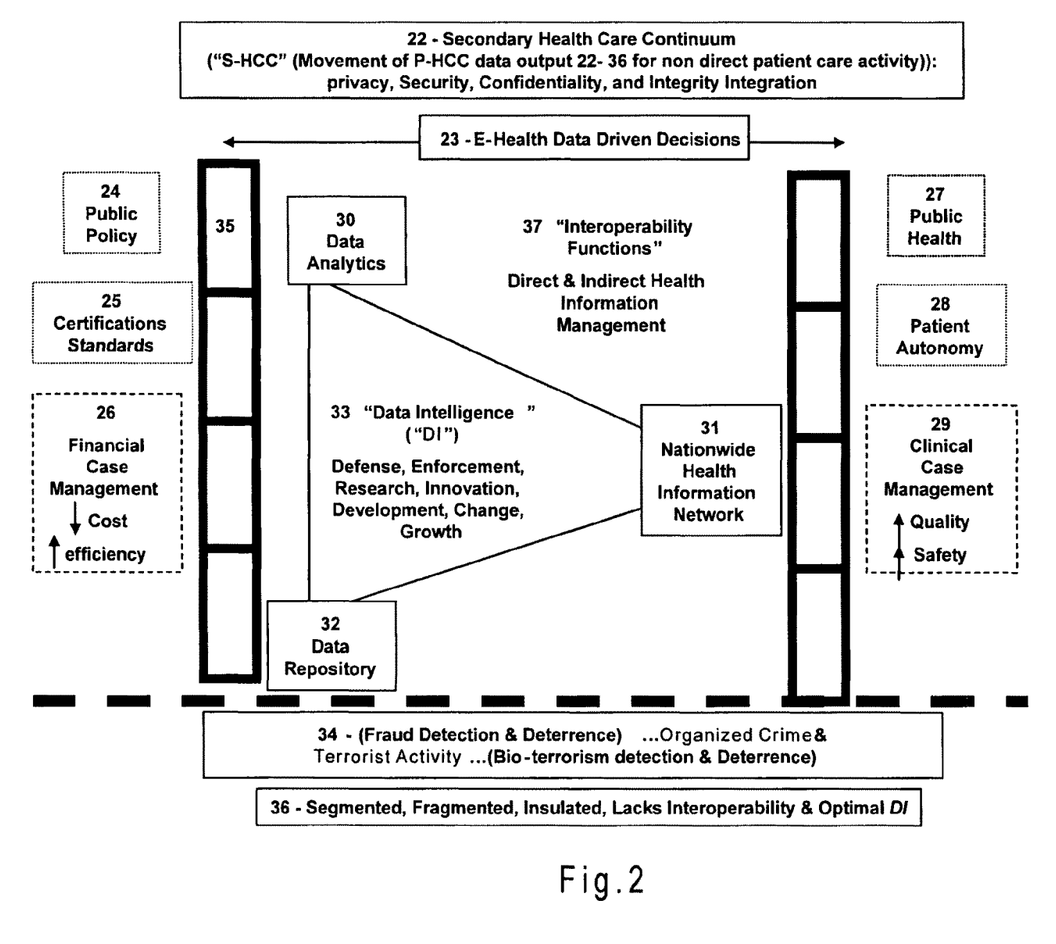
FIG. 2 illustrates the whole and sub parts of the secondary healthcare continuum (S-HCC) of intermittent and contemporaneous privacy, security, confidentiality, and integrity information designed to promote optimal data intelligence (DI) in a fragmented environment that lacks interoperability.

FIG. 2 illustrates the operational mechanisms necessary for and policy standards applicable to resources to provide comprehensive data feeds into the electronic health record case management system. These include public and private data standards 24, 25 and 27. It is desirable to provide patient autonomous access 28 to retrieve data intelligence from the system. Contemporaneous sets of algorithms pertaining to items 30-34 are required to process critical data driven decisions. For example, the market policy on mitigation of medical identity theft is not developed. If a perpetrator is identified through data analytics the potential exposure and identification of other victims and providers who have been compromised can be stored in 30-34. The benefit of this process is compromise of the patient by having convoluted health information such as the wrong blood type and theft of dollars from a patients benefit plan. Where existing barriers 35 within the healthcare continuum and the nature 36 of the data in the healthcare continuum's data environment are recognized, this invention breaks down these barriers and creates transparent electronic data-driven decisions 23 within the healthcare continuum. The algorithmic data-driven decisions of the system have a dual impact 26 on financial case management, namely a decrease in costs and an increase in efficiency. The data-driven decisions similarly have a dual impact 29 on clinical case management, namely, an increase in both service quality and patient safety. In the Lipitor example, the case manager can use the system of the invention to provide transparent pricing data and take corrective actions in medical records to differentiate lab tests associated with counterfeit medication versus laboratory tests associated with a legitimate product, thus improving quality of care and patient safety.

Figure 3:
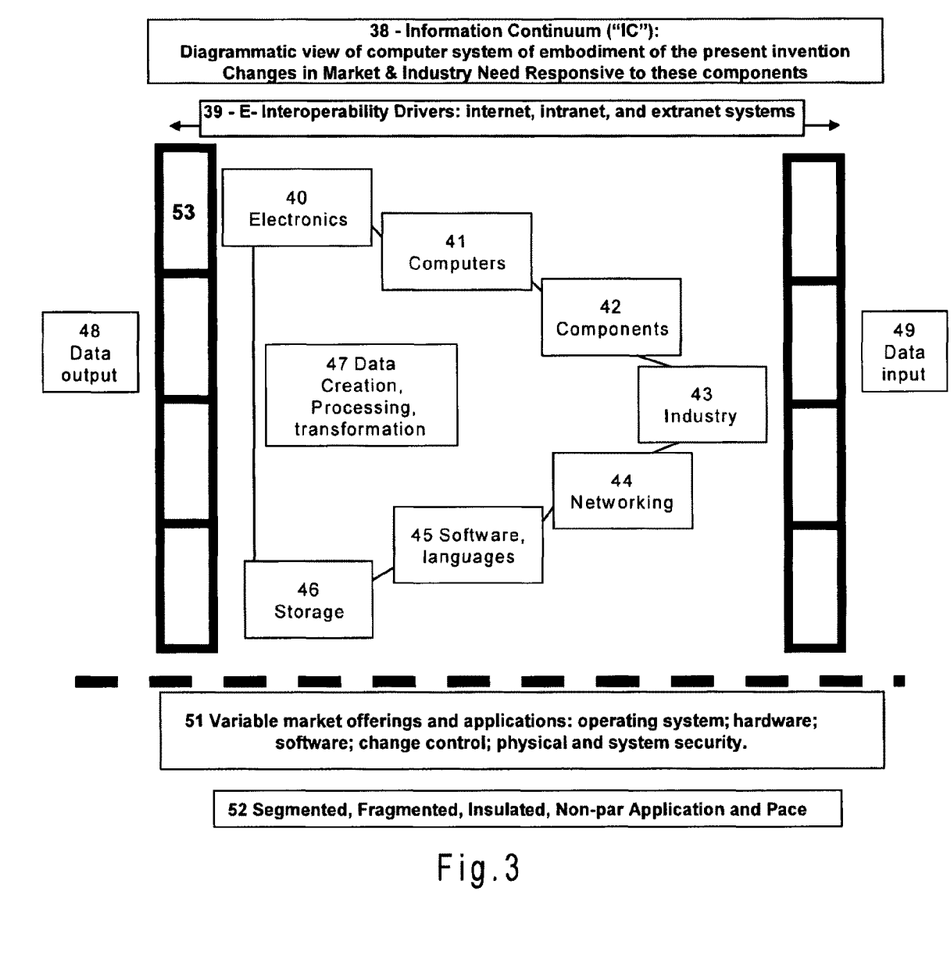
FIG. 3 illustrates the whole and subparts critical components of the information continuum (IC) intermittent and contemporaneous components necessary to transfer and create data as it relates to the primary and secondary healthcare continuums.

FIG. 3 illustrates the technological components necessary to provide comprehensive data feeds into the electronic health record case management system, including software and hardware components 40-46 within the information continuum infrastructure. The system reflects the fact 51 that market players utilize a variety of non-uniform components to manage data. The set of algorithms for data creation, processing and transformation 47 include data input 48 and data output 49 that feed the data into and out of the electronic health record case management system. Electronic interoperability drivers 39 may include the internet as well as intranet and extranet systems. The system recognizes existing barriers 53 within the healthcare continuum and accounts for the nature 52 of the data in the healthcare continuum's data environment.

Figure 4:
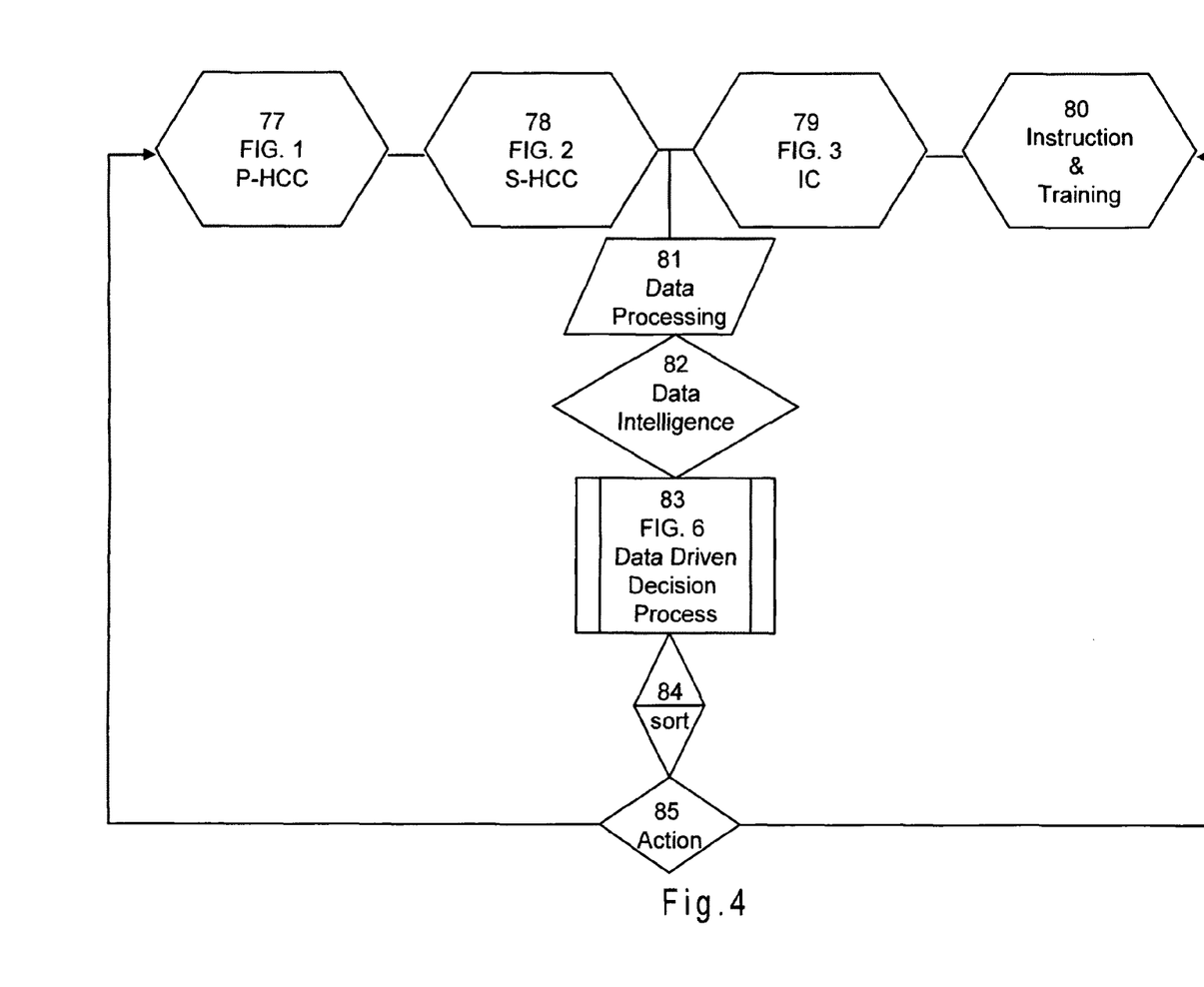
FIG. 4 illustrates the whole and subparts concurrent entwined data attributes (from FIG. 1-4) with intermittent and contemporaneous processing mechanics.

FIG. 4 illustrates a decision matrix required for effective data-driven case management decisions based on the information generated by the data resources identified within the primary healthcare continuum of FIG. 1, the mechanisms and standards identified in the secondary healthcare continuum of FIG. 2, and the components identified in the information continuum infrastructure of FIG. 3. The decision matrix reflects how the electronic health record case management system integrates independent decision trees into its engine. The method of the electronic health record case management system collects data from sources 77-80 for data processing at step 81. Data processing 81 generates intelligent data 82 for data-driven decision processing 83, as detailed in FIG. 5, discussed below. Data is then sorted at step 84 for case management action at step 85.

Figure 5:
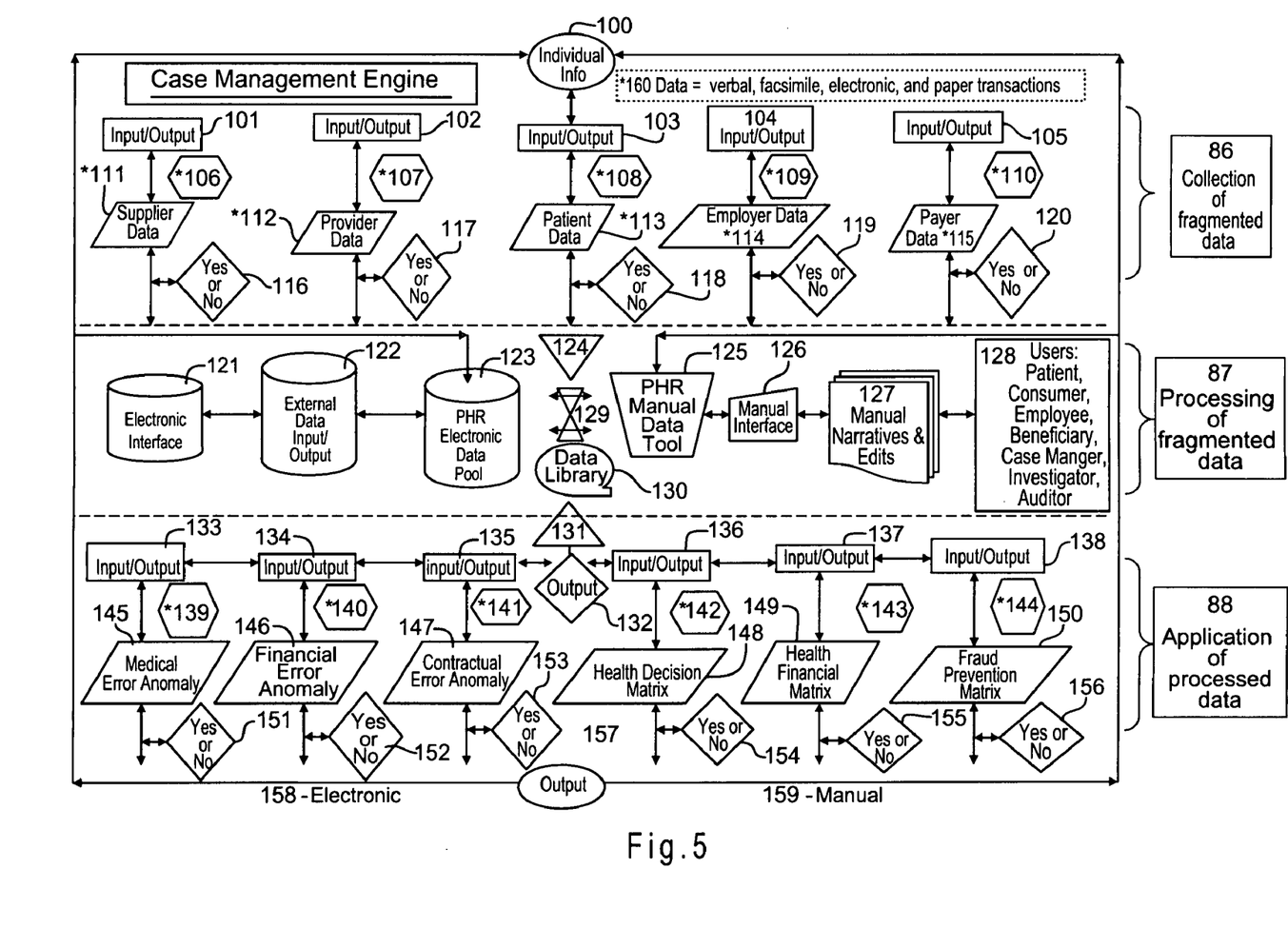
FIG. 5 illustrates the whole and subparts of case management data-driven with intermittent and contemporaneous decision processing mechanics.
Figure 7:
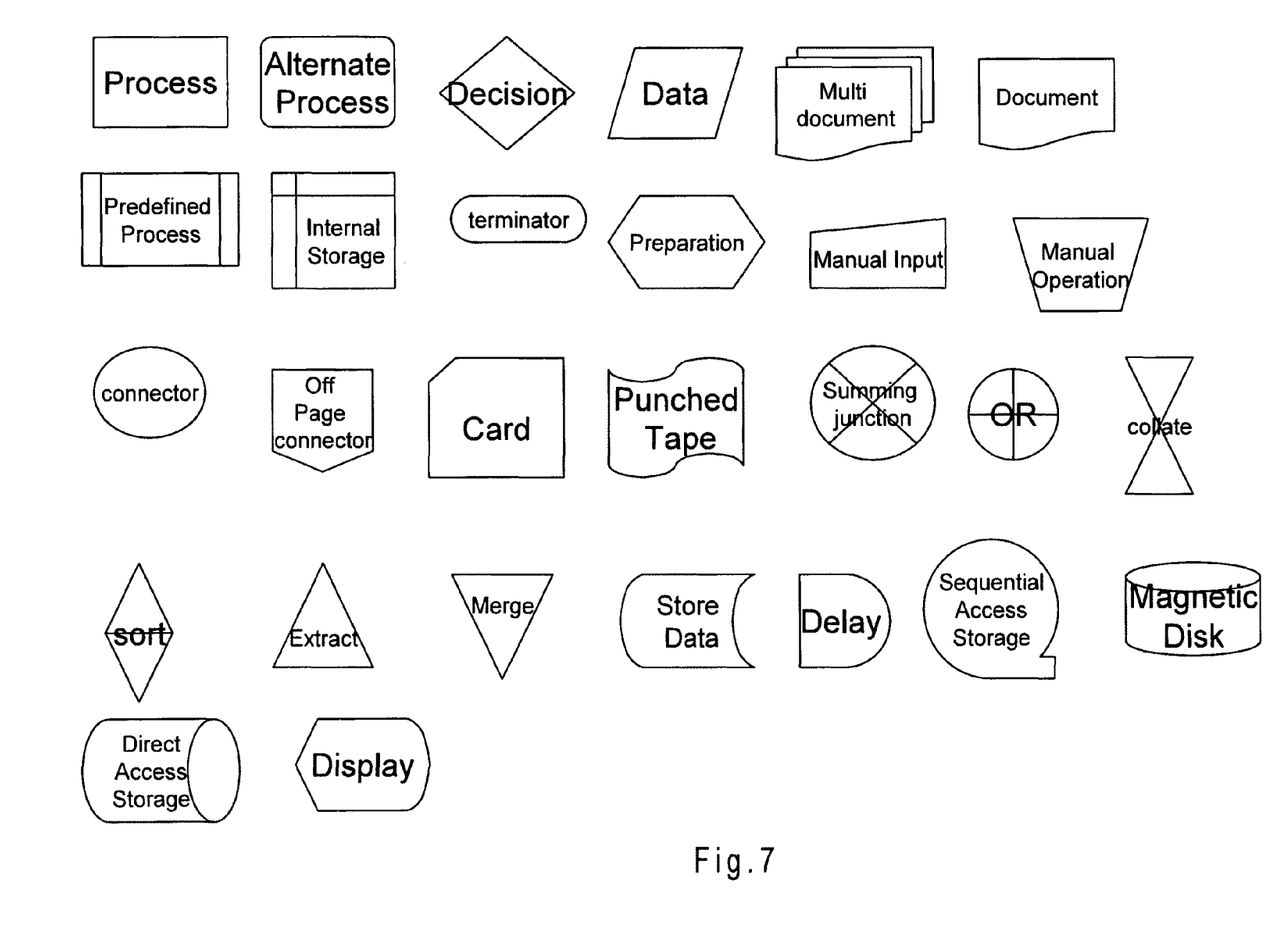
FIG. 7 is an illustration of a key defining symbols used in FIG. 5.

FIG. 5 illustrates the data driven case management decision processing mechanics central to the invention's effectiveness. A key defining the symbols used in FIG. 5 is illustrated in FIG. 7. The processes of the case management engine are categorized into three levels, as divided schematically by the dashed lines in FIG. 5. The first level 86 collects fragmented data from various data sources 100-120. The second level 87 processes fragmented data from the first level 86 on behalf of users 128. Data processing creates an electronic data library 130 of organized usable and comprehensive case management information. The third level 88 applies the processed data from the second level 87 using decision-making algorithm engines 145-147 and matrices 148-150; including, for example a defined medical error anomalies engine 145; a financial error anomalies engine 146; a contractual error anomalies engine 147; a health decision matrix 148; a health financial matrix 149; and a fraud prevention/mitigation matrix 150.

In first level 86 for collection of fragmented data as shown in FIG. 5, supplier data 111, provider data 112, patient data 113, employer data 114, and payer data 115 enter the system at input/output points 101-105, respectively. The data 111-115 may enter via an oral, facsimile, electronic, paper or any other form of communicative transaction. For each respective input/output point 101-105, options then may be listed by a corresponding decision matrix 106-110 for selection by a user. The user's selection of whether and where to route the data next feeds a corresponding decision point 116-120, which may result in routing the data into any of electronic media 121-123, manual media 125-128, or merge point 124 as shown in FIG. 5.

In second level 87 for processing of the fragmented data as shown in FIG. 5, electronic data library 130 houses current and future adjusted algorithm types that process the data elements that are received from various sources. For example, data may be received via an electronic interface 121. Data may be manually entered via external data input/output sources 122, which may include a mouse, keyboard, touch screen, or any other suitable electronic input device. Data received from a personal health record ("PHR") electronic data pool 123 may be processed. PHR manual data is received via PHR manual data tool 125. Manual interface 126 for entry of manually-input data into the system receives the output of PHR manual data tool 125 as well as manual narratives and edits 127 and the list of identified users 128. Data from each of media 121-123 and 125-128 is fed into merge point 124 and converted into a unified electronic format. Then, the data is filtered through filter 129. The sorted unified electronic data from filter 129 is stored in data library 130, which may take the physical form of data logic stored on a memory chip or other device, hard disk, CD-ROM disk, DVD-ROM disk, floppy disk, or any other suitable computer readable medium.

A processor then carries out algorithms to route the data from data library 130 to the appropriate input/output links 133 through 138. These algorithms may include, but are not limited to, simple recursive algorithms (when large problems require simplification to smaller problems for resolution), back-tracking algorithms (when the need requires the elimination of multiple solutions without examination of each solution), "divide-and-conquer" algorithms (when a problem needs to be subdivided and broken down into smaller problems), dynamic programming algorithms (problem solving is required when overlapping solutions are presented), "greedy" algorithms (used when the need to find the most optimal solution is presented), "branch and bound" algorithms (general search method is required), "brute force" algorithms (used when an enumeration of possible options are required for review), and randomized algorithms (used for quality assurance to review all data processed for any potential anomalies). The algorithm is selected based on the decision matrix issue output in the case management function. If the case manager is looking for all possible options, "brute force" would be selected. In the continuation of pharmaceutical related examples, if post surgical care high pain response and increased post operative pneumonia were the clinical subject, the following hypothetical scenario could be an example of a brute force output: A group of post surgical patients in one area of a hospital had a sudden increase in post surgical exercise and resulting pneumonia complications. The fragmented data 87 included the patients associated with one practitioner. The application of the data 88 listed clinical baseline patient assessments in addition to provider competence. The algorithms generated clinical data parameters in addition to parameters to evaluate substance abuse by the practitioner. The patients had a consistent non-response to pain medications provided.

Third level 88 applies the processed data using decision making algorithm engines retrieval link 131 and output return link 132. Specifically, input/output links 133-138 take the processed data from the algorithms to select an appropriate anomaly engine 145-147 or decision matrix 148-150. That selection will lead to the appropriate link. For example, the processed data library information from data library 130 will be filtered in filters 131 and 132, as described in the following paragraphs. If processed data indicating a medical error is identified, filters 131 and 132 will filter the appropriate data output based on filtering criteria and route the data to input/output link 133 to evaluate the medical error in medical error anomaly engine 145. For example, if the case is that of a patient receiving incompatible medications, filters 131 and 132 will identify all relevant clinical or financial data involving the medications and direct an appropriate list of options for mitigation of damages from the medication error to be displayed to the user on a screen or printout. For example, if an overdose of valium is identified, one option displayed may be to administer a reversal medication. In the above case of the practitioner with substance abuse, alternatives may be listed to mitigate damage to the patients who were not being treated properly for post surgical pain, such as administering pain medication or changing the pain medication or dosage administered. The lack of pain management may have prevented the patient from properly exercising after surgery which in turn resulted in a higher pneumonia occurrence rate. The system of the present invention would identify and alert the case manager to the etiology of a patient not receiving the appropriate pain medication, thus permitting the case manager to evaluate the circumstances and take the most appropriate action.

A similar pattern will occur for a financial error anomaly. In other words, filters 130-132 are used to identify the appropriate filter of "medical error" for the case manager to work with the affected consumer. The relevant data elements from the prior links will be filtered to the appropriate anomaly engine 145-147 or decision matrix 148-150, specifically noted as medical error anomaly engine 145; financial error anomaly engine 146; contractual error anomaly engine 147; health decision matrix 148; health financial matrix 149; or fraud prevention matrix 150. This electronic tool is currently not provided in the market in any case management role or tool. That output may result in the following data flows:

Filter Flag "Medical Anomaly" will route the data in this format: The relevant data output will be routed through input/output 133 which will lead to decision matrix 139 listing the options for selection by the user. The result of the decision selected by the user will be noted in medical error anomaly data 145 and classified as "medical error anomaly." The decision selection and results by the user feed decision point 151. The applied user decision will feed an output 157 and the system will recycle that output back to first level 86 input 100 via electronic link 158 or manual link 159.

Filter Flag "financial error anomaly" will route the data in this format: The relevant data output will be routed through input/output 134 which will lead to decision matrix 140 listing the options for selection by the user. The result of the decision selected by the user will be noted in financial error anomaly data 146 and classified as "financial error anomaly". The decision selection and results by the user feed decision point 152. The applied user decision will feed output 157 and the system will recycle that output back to first level 86 input 100 via electronic link 158 or manual link 159.

Filter Flag "contractual error anomaly" will route the data in this format: The relevant data output will be routed through input/output 135 which will lead to decision matrix 141 listing the options for selection by the user. The result of the decision selected by the user will be noted in contractual error anomaly data 147 and classified "contractual error anomaly." The decision selection and results by the user feed decision point 153. The applied user decision will feed output 157 and the system will recycle that output back to first level 86 input 100 via electronic link 158 or manual link 159.

Filter Flag "health decision matrix" will route the data in this format: The relevant data output will be routed through input/output 136 which will lead to decision matrix 142 listing the options for selection by the user. The result of the decision selected by the user will be noted in health decision matrix data 148 and classified "health decision matrix". The decision selection and results by the user feed decision point 154. The applied user decision will feed output 157 and the system will recycle that output back to first level 86 input 100 via electronic link 158 or manual link 159.

Filter Flag "health financial matrix" will route the data in this format: The relevant data output will be routed through input/output 137 which will lead to decision matrix 143 listing the options for selection by the user. The result of the decision selected by the user will be noted in health financial matrix data 149 and classified "health financial matrix". The decision selection and results by the user feed decision point 155. The applied user decision will feed output 157 and the system will recycle that output back to first level 86 input 100 via electronic link 158 or manual link 159.

Filter Flag "fraud prevention/mitigation matrix" will route the data in this format: The relevant data output will be routed through input/output 138 which will lead to decision matrix 144 listing the options for selection by the user. The result of the decision selected by the user will be noted in fraud prevention/mitigation matrix data 150 and classified "fraud prevention/mitigation matrix." The decision selection and results by the user feed decision point 156. The applied user decision will feed output 157 and the system will recycle the output back to first level 86 input 100 via electronic link 158 or manual link 159.

All examples may impact the future adjustments to the algorithms contained in data library 130 as output is fed back to first level input 100 via electronic link 158 or manual link 159 from output 157.

Critical Data Driven Case Management elements include, but are not limited to, individually identifiable patient information initiated at step 100 and filtered throughout the system illustrated in FIG. 5, e.g.:

Item #Description for Data Set 1
1. Name of patient
2. All geographic subdivisions smaller than a state, including street address, city, county, precinct, ZIP Code, and their equivalent geographical codes, except for the initial three digits of a ZIP Code if, according to the current publicly available data from the Bureau of the Census:

a. The geographic unit formed by combining all ZIP Codes with the same three initial digits contains more than 20,000 people
b. The initial three digits of a ZIP Code for all such geographic units containing 20,000 or fewer people are changed to 000
3. All elements of dates (except year) for dates directly related to an individual, including birth date, admission date, discharge date, date of death; and all ages over 89 and all elements of dates (including year) indicative of such age, except that such ages and elements may be aggregated into a single category of age 90 or older
4. Telephone numbers
5. Facsimile numbers
6. Email addresses
7. Social security numbers
8. Medical record numbers
9. Health plan beneficiary numbers
10. Account numbers
11. Certificate/license numbers.
12. Vehicle identifiers and serial numbers, including license plate numbers
13. Device identifiers and serial numbers
14. Web universal resource locators (URLs)
15. Internet protocol (IP) address numbers
16. Biometric identifiers, including fingerprints and voiceprints.
17. Full-face photographic images and any comparable images
18. Any other unique identifying number, characteristic, or code, unless otherwise permitted by the Privacy Critical Data Anomaly Output data elements include but are not limited to professional claims and related health information data initiated at first level 86 and filtered throughout the system illustrated in FIG. 5, e.g.:

Item #Description for Data Set 2
1 Medicare, Medicaid, Champus, Champ VA, Group, FECA, Other
1a Insured's ID Number
2 Patient's Name
3 Patient's Date of Birth
4 Insured's Name
5 Patient's Address
6 Patient Relationship to Insured
7 Insured's Address
8 Patient Status
9 Other Insured's Name
9a Other insured's Policy or Group Number
9b Other Insured's Date of Birth
9c Employer's Name or School Name
9d Insurance Plan Name or Program Name
10 Is Patient's Condition Related To:
10a Employment?
10b Auto accident?
10c Other accident?
11 Insured's Policy Group or FECA Number
11a Insured's Date of Birth
11b Employer's Name or School Name
11c Insurance Plan Name or Program Name
11d Is there another health benefit plan?
12 Patient's or Authorized Person's Signature
13 Insured's or Authorized Person's Signature
14 Date of Current Illness, Injury or Pregnancy
15 Date of Same or Similar Illness
16 Dates patient unable to work in current occupation
17 Name of referring physician or other source
17a ID number of referring physician
18 Hospitalization dates related to current services
19 Reserved for local use
20 Outside Lab?
21 Diagnosis or nature of illness or injury
22 Medicaid Resubmission Code and Original Ref No.
23 Prior Authorization Number
24a Dates of Service
24b Place of Service
24c Type of Service
24d Procedures, Services or Supplies
24e Diagnosis code
24f $ Charges
24g Days or Units
24h EPSDT Family Plan
24i EMG
24j COB
24k Reserved for local use
25 Federal Tax ID Number
26 Patient's Account Number
27 Accept Assignment?
28 Total Charge
29 Amount Paid
30 Balance Due
31 Signature of Physician or Supplier
32 Name and Address of Facility where services were rendered
33 Physician's, Supplier's Billing Name, Address, Zip Code and Phone Number Critical Data Anomaly Output data elements include but are not limited to facility claims and related health information data initiated at first level 86 and filtered throughout the system illustrated in FIG. 5, e.g.:

Item #Description for Data Set 3
1 Hospital Name and Address
2 Payee Address
3.a Patient Control Number
3.b Medical Record Number
4 Type of Bill
5 Federal Tax Number
6 Statement Covers Period from . . . through . . .
7 Administrative Necessary Days
8 Name on Medical Identification card
9 Patient Address
10 Birth date
11 Sex
12 Admission Date
13 Admission Hour
14 Admit Type
15 Source of Admission
16 Discharge Hour
17 Patient Discharge Status
18 Condition Code
19 Condition Code
20 Condition Code
21 Condition Code
22 Condition Code
23 Condition Code
24 Condition Code
25 Condition Code
26 Condition Code
27 Condition Code
28 Condition Code
29 Accident State
30 Accident Date
31 Occurrence Code and Date
32 Occurrence Code and Date
33 Occurrence Code and Date 34 Occurrence Code and Date
35 Occurrence Span Code and Dates
36 Occurrence Span Code and Dates
37 Miscellaneous anomaly
38 Responsible Party Name and Address
39 Value Codes and Amounts
40 Value Codes and Amounts
41 Value Codes and Amounts
42 Revenue Codes
43 Description
44 HCPCS/RATES
45 Service Dates
46 Service Units
47 Total Charges
48 Non-Covered Charges
49 Miscellaneous anomaly
50 Payer
51 Health Plan ID
52 Release of Information
53 Assignment of Benefits
54 Prior Payments
55 Estimated Amount Due
56 National Provider Identifier Billing Provider (NPI)
57 Other Provider Number
58 Insured's Name
59 Patient Relation to Insured
60 Insured Unique Identifier (SSN-HIC-ID No)
61 Group Name
62 Insurance Group Number
63 Treatment Authorization Codes
64 Document Control Number
65 Employer Name
66 Diagnosis and Procedure code qualifier
67 A-Q Other Diagnosis Codes
68 Admitting Diagnosis Code
69 Diagnosis Code
70 Patient's Reason for Visit
71 PPS Code
72 External Cause of Injury Code
73 Miscellaneous anomaly
74 Principal Procedure Code & Date
74 a-e Other Procedure Codes
75 Miscellaneous anomaly
76 Attending Provider Name and Identifier Number
77 Operating Physician Name and Identifier
78 Other Provider Name and Identifier
79 Other Provider Name and Identifier
80 Remark Field
81 Corresponding Tax ID Number
82 Other Physician ID Critical Data Anomaly Output data elements include but are not limited to dental, vision, pharmaceutical, wellness programs, consumer directed health plan, and non-traditional provider claims and related health information data initiated at first level 86 and filtered throughout the system illustrated in FIG. 5, e.g.:

Item Description for Data Set #4
Item# Description—Dental
1 Statement of transaction—request for service or service provided
2 Pre-authorization number
3 Insurance company name address
4 Claim dental or medical
5 Name of policy holder
6 Patient Date of Birth
7 Patient Gender
8 Policy subscriber ID number
9 Plan group number
10 Patient relationship to insured
11 Other insurance coverage
12 Policy holder name and address
13 Insured Date of Birth
14 Policy Holder Gender
15 Policy Holder ID
16 Plan group number
17 Employer Name and Address
18 Patient relationship to insured
19 Student Status
20 Name and address
21 Patient Date of Birth
22 Patient Gender
23 Patient ID number SSN
24 Procedure Date
25 Areas of oral cavity
26 Tooth System
27 Tooth numbers or letters
28 Tooth Surface
29 Procedure Code
30 Description
31 Fee
32 Other Fees
33 Total Fees
34 Missing tooth information
35 Remarks
36 patient authorizations
37 subscriber authorization
38 Place of treatment
39 Number of enclosures
40 treatments for orthodontics
41 dates appliance placed
42 months of treatment remaining
43 replacement of prosthesis
44 date of prior placement
45 treatments resulting from
46 date of accident
47 Auto Accident State
48 Provider name and address
49 National Provider Identifier
50 License number
51 SSN or Tax ID number
52 Phone Number
53 Additional Provider number
54 Provider authorization
55 NPI
56 License number
Item # Description-Pharmacy
1 Rx Group
2 Member ID
3 Address information
4 Patient Name
5 Patient Identifier
6 Pharmacy Name
7 Pharmacy Identifier
8 Drug NDC #
9 Date Filled
10 Quantity Filled
11 Total Charges
Item # Description-Durable Medical Equipment
1 Product name
2 Product Number
3 Nature of illness
4 Nature of injury
5 Date of occurrence
6 Total charges 7 Name of provider
8 Provider Identifier
9 Provider Address
10 Group number Anomaly engines 145-147 and decision matrices 148-150 yield the output of data driven case management decisions to decision points 151-156, respectively. For example, any medical anomaly related output occurs at decision point 151, any financial anomaly related output occurs at decision point 152, etc.

Illustrative examples of the output of the anomaly engines 145-147 are as follows: (1) a medical error such as a male patient (indicated by data element "sex") with a procedure code (data element) of "hysterectomy" as determined by medical error anomaly engine 145 would result in a medical anomaly at decision point 151; (2) a financial error such as data element "Total Charges" of "1,000" for quantity "Service Units" one unit of Tylenol as determined by financial error anomaly engine 146 would result in a financial anomaly at decision point 152; (3) a contractual error anomaly (for example data element "diagnosis code" of "cosmetic procedure" and "benefits paid" for non-covered item) as determined by contractual error anomaly engine 147 would result in a contractual anomaly at decision point 153.

Illustrative examples of the output of the decision matrices 148-150 are as follows: (1) at decision point 154, for any health decision matrix 148 decision (for example data element "age" of "88" and data element "procedure" of "flu vaccine" for a wellness plan); (2) at decision point 155 for any health financial matrix 149 decision (for example data elements "service units" and benefit plan approval "10" to determine source of funding); (3) at decision point 156 for any fraud prevention matrix 150 decision of the occurrence potentially fraudulent activity (for example, medical identity theft can occur with data element "SSN" ID and "patient address" conflicts).

The output of decision points 151, 152, 153, 154, 155, and 156 is filtered through third level output 157 and linked back to first level input 100 through a manual process 159 or an electronic process 158 to provide the learning aspect of the data decision matrices.

Figure 6:
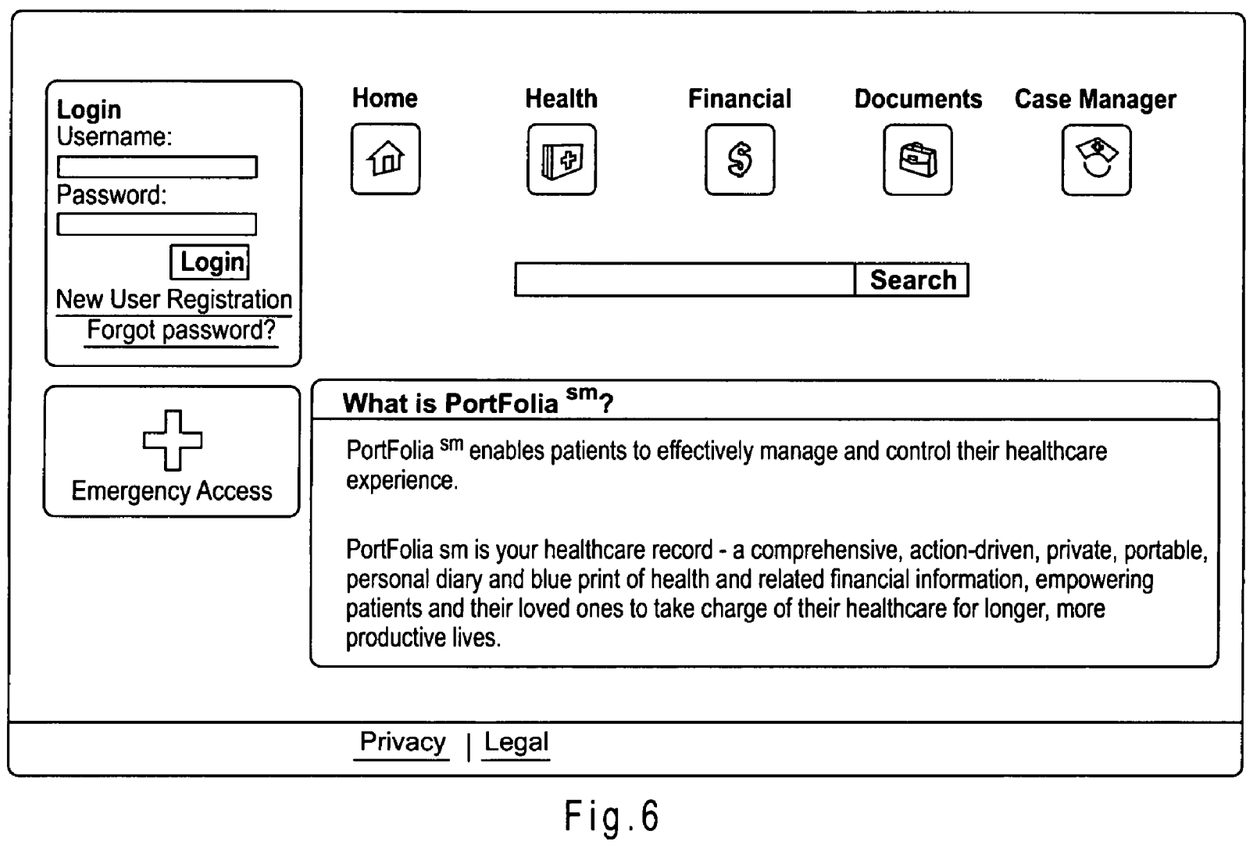
FIG. 6 illustrates the whole and subparts of an exemplary initial electronic health record case management system with intermittent and contemporaneous user interface screen.

FIG. 6 illustrates an exemplary initial user interface screen display for the user electronic health record case management system. The option button labeled "Home" collects at minimum the information in Data Set 1. The option buttons labeled "Health," "Financial" and "Documents" collect from a variety of sources information contained in Data Sets 1 and 2. The last button labeled "Case Manager" houses the activity of the case management engine as shown in FIG. 5. The user interface displays various options provided by the case management engine for selection by the user as described above and permits user input in response thereto, and displays results generated by the case management engine.

What is claimed is:

1. A system for identifying and addressing anomalies in a customer's health records comprising
a device encoded with logic;
a display;
an input device;
a data storage device; and
one or more processors adapted to execute the logic to:
collect fragmented health data pertaining to the customer from a plurality of data sources including patients, health benefit program sponsors, healthcare payers, healthcare providers, and healthcare vendors;
convert the fragmented data to a unified electronic format;
merge the converted data into a data library in the data storage device;
apply an algorithm to the unified and merged data to identify data indicating an anomaly;
route the anomalous data to an appropriate one of a plurality of decision matrices and anomaly engines stored in the system to be executed by the processor, the appropriate decision matrix or anomaly engine corresponding to a type of anomaly identified and to a list of a plurality of options for addressing the type of anomaly;
output a message to a user indicating the type of anomaly and listing the plurality of options for addressing the type of anomaly on the display;
receive a decision selected by the user operating the input device; and
store the decision selected by the user in the data library,
further comprising an alert component configured to access public health data indicating that a medication type has been stolen from a pharmaceutical inventory or counterfeited and to display an alert on the display if the customer's health data indicates use of the medication type by the customer in the past, present or future.

2. The system of claim 1, the plurality of decision matrices and anomaly engines including a medical error anomaly engine, a financial error anomaly engine, a contractual error anomaly engine, a health decision matrix, a health financial matrix, and a fraud prevention matrix.

3. The system of claim 1, the logic including data filter logic, the one or more processors adapted to execute the data filter logic to exclude segmented, fragmented, insulated, and non-transparent service and price data from the data library.

4. A method of identifying and correcting medical anomalies in a customer's health records comprising
providing a system including a display, an input device, a data storage device, and a device encoded with and adapted to execute
logic to collect fragmented health data pertaining to the customer from a plurality of data sources including patients, health benefit program sponsors, healthcare payers, healthcare providers, and healthcare vendors;
logic to convert the fragmented data to a unified electronic format;
logic to merge the converted data into a data library in the data storage device;
logic to apply an algorithm to the unified and merged data to identify data indicating a medical anomaly;
logic to output a message to a user on the display notifying the user of the medical anomaly and listing a plurality of options for addressing the medical anomaly;
logic to receive a decision selected by the user operating the input device;
logic to store the decision selected by the user in the data library; and
alert component logic to access public health data indicating that a medication type has been stolen from a pharmaceutical inventory or counterfeited and to display an alert on the display if the customers health data indicates use of the medication type by the customer in the past, present or future;
receiving a message from the system on the display device indicating that a medical anomaly in the customer's health records was identified and listing options for addressing the medical anomaly;
selecting an option from the listed options and inputting the selection into the input device; and providing treatment to the customer to correct the medical anomaly in accordance with the selected option.

5. A system for identifying and addressing anomalies in a customers health records comprising
- a device encoded with logic;
- a display;
- an input device;
- a data storage device; and
- one or more processors adapted to execute the logic to:
  - collect fragmented health data pertaining to the customer from a plurality of data sources including patients, health benefit program sponsors, healthcare payers, healthcare providers, and healthcare vendors;
  - convert the fragmented data to a unified electronic format;
  - merge the converted data into a data library in the data storage device;
  - apply an algorithm to the unified and merged data to identify data indicating an anomaly;
  - route the anomalous data to an appropriate one of a plurality of decision matrices and anomaly engines stored in the system to be executed by the processor, the appropriate decision matrix or anomaly engine corresponding to a type of anomaly identified and to a list of a plurality of options for addressing the type of anomaly;
  - output a message to a user indicating the type of anomaly and listing the plurality of options for addressing the type of anomaly on the display;
  - receive a decision selected by the user operating the input device; and
  - store the decision selected by the user in the data library,
  - further comprising an alert component configured to access public health data indicating that a perpetrator of medical identity theft has been identified and to display an alert on the display if the medical identity theft has compromised the customer's health data or the health data of a provider of healthcare to the customer.

6. The system of claim 5, the plurality of decision matrices and anomaly engines including a medical error anomaly engine, a financial error anomaly engine, a contractual error anomaly engine, a health decision matrix, a health financial matrix, and a fraud prevention matrix.

7. The system of claim 5, the logic including data filter logic, the one or more processors adapted to execute the data filter logic to exclude segmented, fragmented, insulated, and non-transparent service and price data from the data library.

8. A method of identifying and correcting medical anomalies in a customer's health records comprising
- providing a system including a display, an input device, a data storage device, and a device encoded with and adapted to execute
  - logic to collect fragmented health data pertaining to the customer from a plurality of data sources including patients, health benefit program sponsors, healthcare payers, healthcare providers, and healthcare vendors;
  - logic to convert the fragmented data to a unified electronic format;
  - logic to merge the converted data into a data library in the data storage device;
  - logic to apply an algorithm to the unified and merged data to identify data indicating a medical anomaly;
  - logic to output a message to a user on the display notifying the user of the medical anomaly and listing a plurality of options for addressing the medical anomaly;
  - logic to receive a decision selected by the user operating the input device;
  - logic to store the decision selected by the user in the data library; and
  - alert component logic to access public health data indicating that a perpetrator of medical identity theft has been identified and to display an alert on the display if the medical identity theft has compromised the customers health data or the health data of a provider of healthcare to the customer;
- receiving a message from the system on the display device indicating that a medical anomaly in the customer's health records was identified and listing options for addressing the medical anomaly;
- selecting an option from the listed options and inputting the selection into the input device; and
- providing treatment to the customer to correct the medical anomaly in accordance with the selected option.

* * * * *